(12) United States Patent
Parker et al.

(10) Patent No.: US 6,706,019 B1
(45) Date of Patent: Mar. 16, 2004

(54) HYPODERMIC SYRINGES

(76) Inventors: David W. Parker, 4 Kimble Close, Bury, Lancashire (GB), BL8 4QQ; Colin H. Burgess, 45 Holcombe Lee, Ramsbottom, Lancashire (GB), BL0 9QR ( * ) Notice: Subject to any disclaimer, the term of this patent is extended or adjusted under 35 U.S.C. 154(b) by 0 days.

(21) Appl. No.: 09/787,813
(22) PCT Filed: Sep. 22, 1999
(86) PCT No.: PCT/GB99/03170
§ 371 (c)(1),
(2), (4) Date: May 17, 2001
(87) PCT Pub. No.: WO00/18454
PCT Pub. Date: Apr. 6, 2000

(30) Foreign Application Priority Data

Sep. 25, 1998 (GB) ................................. 9820784

(51) Int. Cl.[7] .............................. A61M 5/32; A61M 5/00
(52) U.S. Cl. ...................... 604/198; 604/110; 128/919
(58) Field of Search ........................ 604/198, 192, 604/110, 220, 194, 187; 128/919

(56) References Cited

U.S. PATENT DOCUMENTS

| | | | | |
|---|---|---|---|---|
| 5,114,404 A | * | 5/1992 | Paxton et al. ............... | 604/110 |
| 5,122,118 A | * | 6/1992 | Haber et al. ................ | 128/919 |
| 5,135,511 A | * | 8/1992 | Houghton et al. .......... | 604/218 |
| 5,211,628 A | | 5/1993 | Marshall | |
| 5,324,265 A | | 6/1994 | Murray et al. | |
| 5,344,403 A | | 9/1994 | Lee | |
| 5,378,240 A | * | 1/1995 | Curie et al. ................. | 604/110 |
| 5,423,758 A | * | 6/1995 | Shaw .......................... | 600/576 |
| 5,458,576 A | | 10/1995 | Haber et al. | |
| 5,624,405 A | * | 4/1997 | Futagawa et al. ........... | 604/187 |
| 5,632,733 A | * | 5/1997 | Shaw .......................... | 604/110 |
| 5,782,804 A | * | 7/1998 | McMahon ................... | 128/919 |
| 5,885,257 A | * | 3/1999 | Badger ........................ | 604/110 |
| 5,997,511 A | * | 12/1999 | Curie et al. ................. | 604/110 |
| 6,096,005 A | * | 8/2000 | Botich et al. ............... | 604/110 |

FOREIGN PATENT DOCUMENTS

| | | |
|---|---|---|
| EP | 0 505 330 | 9/1992 |
| EP | 0 636 381 | 2/1995 |
| EP | 0 747 075 | 12/1996 |
| WO | WO90/06146 | 6/1990 |
| WO | WO91/03269 | 3/1991 |
| WO | WO93/07923 | 4/1993 |
| WO | WO95/11713 | 5/1995 |
| WO | WO96/05879 | 2/1996 |
| WO | WO96/27403 | 9/1996 |

* cited by examiner

Primary Examiner—Manuel Mendez
Assistant Examiner—Mark K. Han
(74) Attorney, Agent, or Firm—Nixon & Vanderhye P.C.

(57) ABSTRACT

A disposable hypodermic syringe, which is provided with the needle fitted and sheathed, provides automatic retraction of the needle after use. The syringe may be supplied precharged with an injectant. The completion of the injection stroke attaches the piston to the needle carrier and subsequently dislodges a retaining ring thereby freeing the piston from the plunger and releasing stored energy of a spring or the like to draw the piston and needle carrier into the plunger. The plunger is positively retained inside the housing by the interaction of rings. Alternative methods of locating the needle carrier during use and of attaching the piston to the needle carrier to enable retraction are shown. An alternative method of retaining the piston on the plunger is also shown. A further configuration is shown affording the use of an offset needle. The syringe has optional features to prevent unwanted inward movement of the plunger and to prevent seepage of liquid after use.

26 Claims, 6 Drawing Sheets

HYPODERMIC SYRINGES

This application is the U.S. national phase of International Patent Application No. PCT/GB99/03170, filed Sep. 22, 1999, which designated the U.S.

BACKGROUND OF THE INVENTION

This invention relates to hypodermic syringes.

In the often high pressure conditions of medical work, the accidental puncture or scratch with a needle, commonly known as a needlestick injury, and consequent risk of infection with, for example, HIV or hepatitis is becoming increasingly hazardous to the profession and potentially more costly to health authorities.

Detailed statistics of needlestick injuries are not generally published in the UK but in the USA such information is more readily available. In 1994 there were some 800,000 cases reported of which 16,000 involved infection with HIV. It is estimated that in the USA, these injuries cost, excluding legal or insurance expenses, $1.8 billion pa.

The requirements for a syringe that will prevent needlestick injuries were analysed and listed as follows:
1. Reliability and ease of use.
2. Automatic and complete retraction of the needle after injection.
3. The capability to retract a needle bent intentionally or accidentally.
4. Re-exposure of the needle is impossible.
5. Suitable for production in larger sizes with an offset needle.
6. Supplied with needle fitted and sheathed.
7. Suitable for supply charged with an injectant.
8. Prevention of accidental needle retraction.
9. Low production costs.
10. Firm and compact for safe disposal.

The urgent need to address this problem has been widely acknowledged and many relevant designs tabled. One such design is known from U.S. Pat. No. 5,211,628 and this document discloses a hypodermic syringe including a housing, a plunger, a needle carrier with a needle mounted thereto positionable during assembly of the syringe within the housing with the needle extending therefrom, a sheath mounted to the needle carrier and surrounding the needle, and stored energy means, the plunger and stored energy means being configured such that when the syringe is used and the plunger reaches the needle carrier, it becomes attached thereto and the stored energy in the stored energy means is released to retract the needle carrier and the needle into the housing.

Similar hypodermic syringes having means for retracting the needle into the plunger after use are known from U.S. Pat. No. 5,324,265, EP-A-0505330 and WO91/03269A.

It is also known from U.S. Pat. No. 5,211,628 to provide a method of assembling a hypodermic syringe that includes the steps of mounting a needle to the needle carrier and positioning the needle carrier in the housing such that the needle extends therefrom.

SUMMARY OF THE INVENTION

A hypodermic syringe according to the present invention is provided with a housing configured such that a needle carrier with the needle mounted thereto is positionable during assembly of the syringe within the housing with the needle pre-sheathed.

In a preferred embodiment, the plunger comprises a casing and a piston located and movable within the casing.

Preferably, the stored energy means is a spring co-operating between the piston and the casing and has a releasable retaining means to release stored energy within the spring.

A method of assembling a hypodermic syringe according to the present invention includes the step of mounting a sheath to the needle carrier over the needle before positioning the needle carrier in the housing.

BRIEF DESCRIPTION OF THE DRAWINGS

Embodiments of the invention will now be described, by way of example only and with reference to the accompanying drawings, in which.

The principal components referred to in the following description are:

| Reference No. | Component Title |
| --- | --- |
| 1. | Housing |
| 2. | Plunger |
| 3. | Piston |
| 4. | Spring |
| 5. | 'O' seal (piston) |
| 6. | Retaining ring |
| 7. | Plunger closure piece |
| 8. | Needle carrier |
| 9. | 'O' seal (needle) |
| 10. | Plunger stop |
| 11. | Drip stop |

DETAILED DESCRIPTION OF PREFERRED EMBODIMENTS

Figure 1:
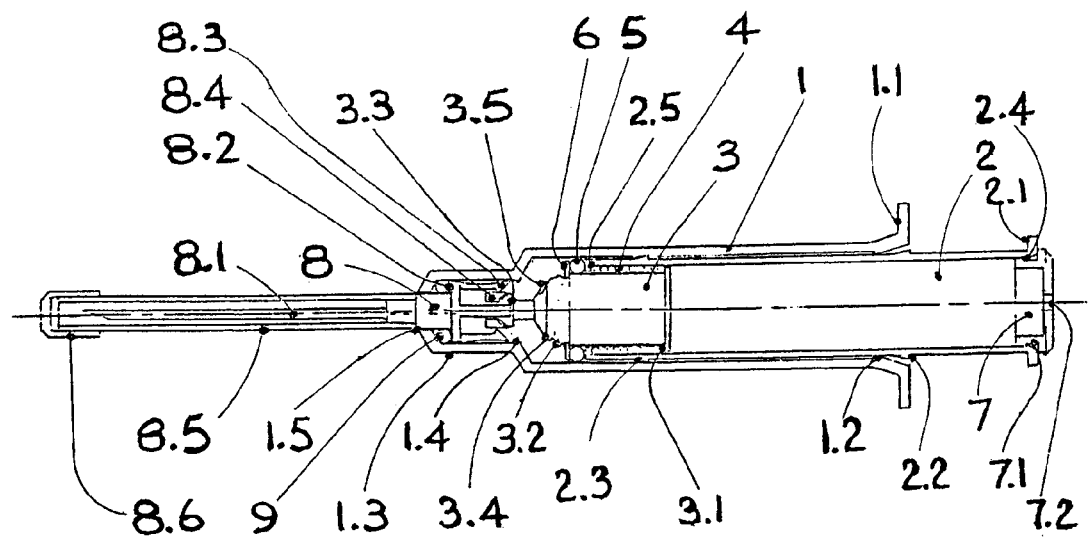
FIG. 1 illustrates a cross-section side elevation of a syringe according to the invention with the plunger about to engage the needle carrier.
Figure 1A:
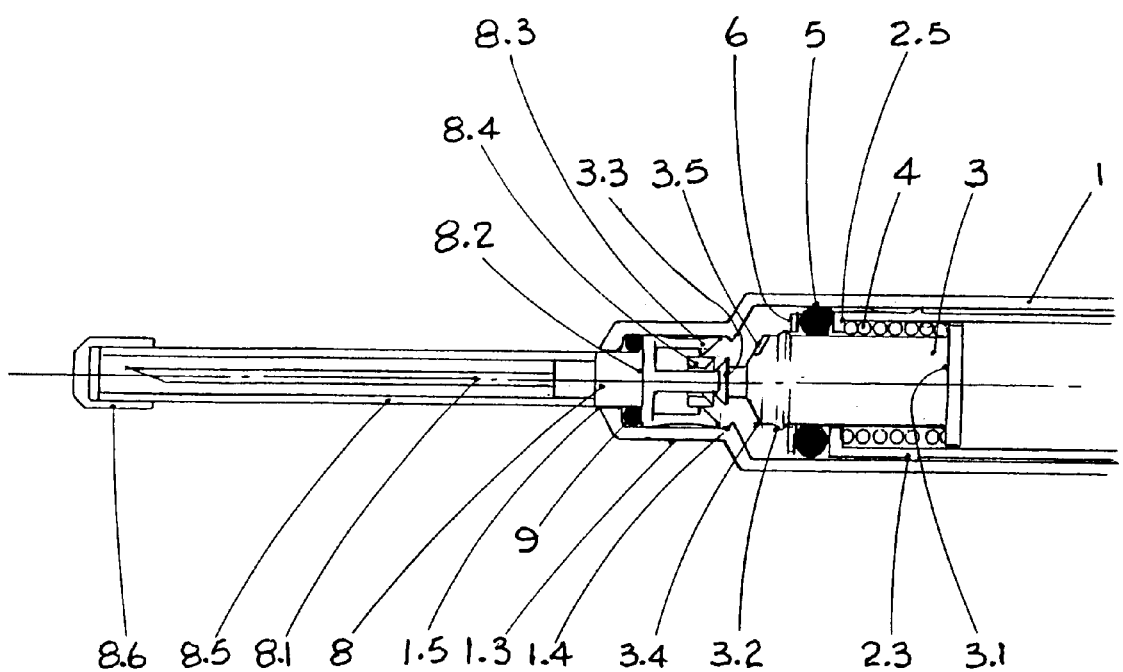
FIG. 1A is an enlarged view of a portion of FIG. 1.

FIGS. 1 and 1A show a typical construction of the syringe. The cylindrical housing (1), graduated as required, carries a flange (1.1) and the open end of the bore has a tapered entry with a locally reduced diameter forming a wedge section ring (1.2).

At the distal end of the housing the diameter is reduced to form a nose (1.3). An internal lip (1.4) is formed at the point where the nose (1.3) meets the main body of the housing (1). The distal end of the nose (1.3) is partly closed leaving an aperture (1.5).

The plunger (2) has on its outer surface a flange (2.1) and two wedge section rings (2.2) and (2.3).

On the inner surface of the plunger (2) at the flanged end is a tapered entry and a locally reduced diameter forming a wedge section ring (2.4).

At the distal end of the plunger (2) is an inward facing flange (2.5).

The piston (3) has an outward facing flange (3.1). The principal diameter of the piston is reduced locally forming a triangular section ring (3.2). The close end of the piston terminates in a head (3.3). The shoulder (3.4) of the piston is grooved to form a fluid bypass (3.5).

The spring (4) is held in compression between flanges (2.5) and (3.1).

The 'O' seal (5) is held between the retaining ring (6) and the flange (2.5). The retaining ring (6) is dislodgeably held in place by the triangular section ring (3.2).

The plunger closure piece (7) has a locally reduced diameter (7.1) and is irreversibly retained by the wedge section ring (2.4) of the plunger (2). An orifice (7.2) is provided in the plunger closure piece.

The needle carrier (8) incorporates a needle (8.1) and a flange (8.2) on which are claw ended arms (8.3). The inwardly sprung arms (8.3) are held in engagement with the lip (1.4) by a spring ring (8.4).

The 'O' seal (9) is located and held in place by the flange.

The needle protective sheath (8.5) is mounted on the needle carrier (8) and is of a lesser diameter than the aperture (1.5). The end cap (8.6) fits over the needle protective sheath (8.5) to form an air-tight seal and is of a larger diameter than the aperture (1.5).

Figure 3:
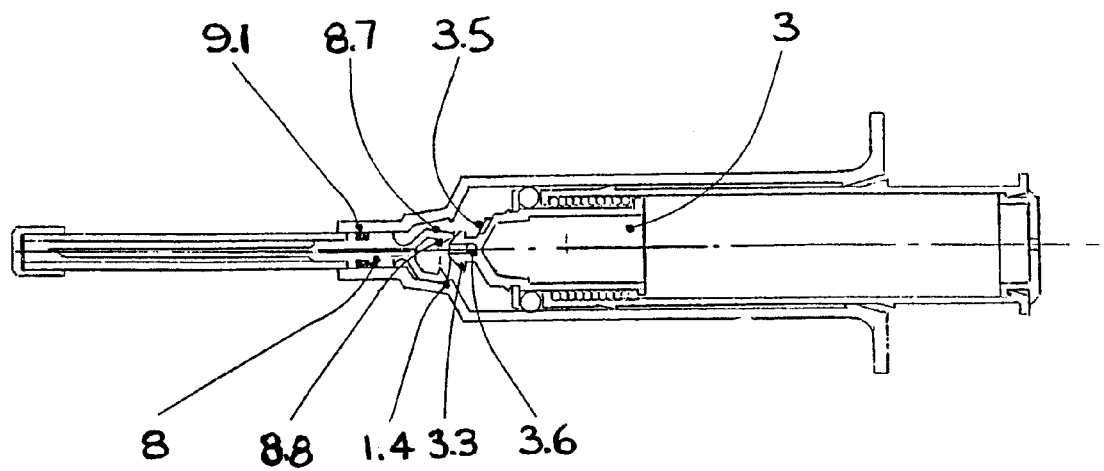
FIG. 3 illustrates a second embodiment of the syringe according to the invention in which the plunger is about to engage the needle carrier.
Figure 4:
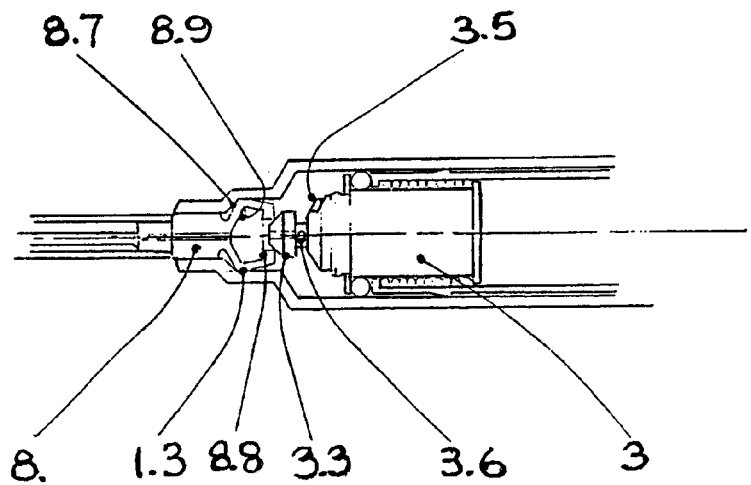
FIG. 4 illustrates a third embodiment of the syringe in which the plunger is about to engage the needle carrier.
Figure 5:
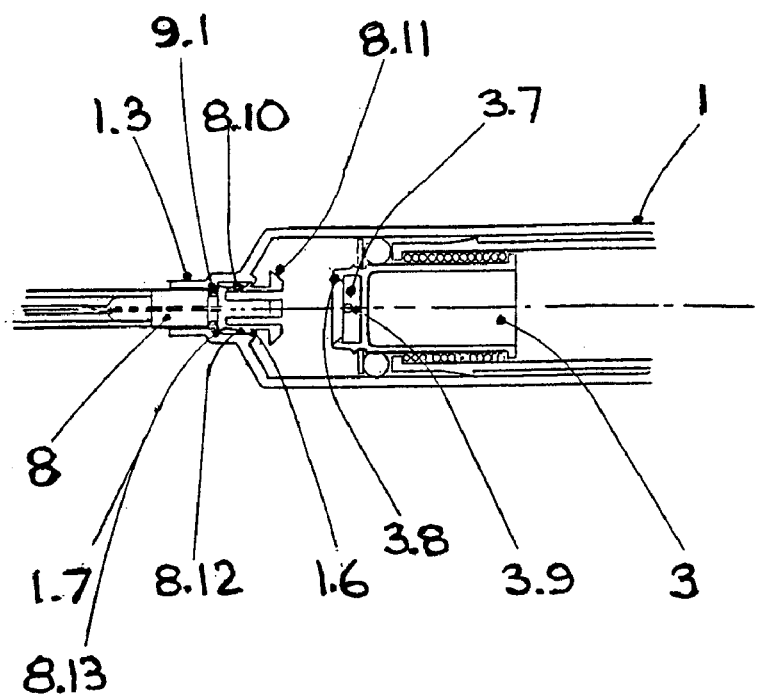
FIG. 5 illustrates a fourth embodiment of the syringe in which the plunger is about to engage the needle carrier.

FIGS. 3, 4 and 5 show alternative constructions of the needle retention and pick up means.

FIG. 3 shows a needle carrier (8) which has a cup (8.7) displaced from the centre line and lodged behind the lip (1.4). The open end of the cup has a retaining lip (8.8). An 'O' seal (9.1) is located in the needle carrier (8). The piston (3) has a fluid bypass (3.5). The piston head (3.3) has a fluid passage (3.6).

FIG. 4 shows a needle carrier (8) in which the cup (8.7) is in firm ring contact with the cylindrical portion of the nose (1.3). No separate seal is used. The closed end of the cup is dished (8.9). The open end of the cup has a retaining lip (8.8). The piston (3) has a fluid bypass (3.5). The piston head (3.3) has a fluid passage (3.6).

FIG. 5 shows a needle carrier (8) with outwardly sprung arms (8.10). The arms have claw ends (8.11) and catches (8.12) that engage with an internal lip (1.6). A flange (8.13) abuts an internal shoulder (1.7) of the nose (1.3). An 'O' seal (9.1) is located in the needle carrier. The piston (3) has a cup end (3.7) with an inwardly facing lip (3.8) and a fluid passage (3.9).

Figure 6:
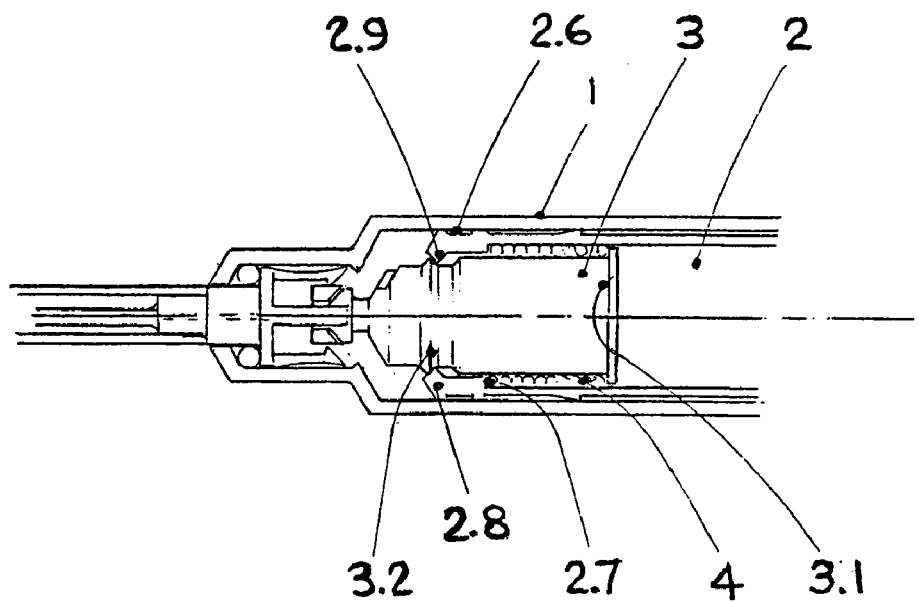
FIG. 6 illustrates a fifth embodiment of the syringe in which the plunger is about to engage the needle carrier.

FIG. 6 shows a construction with an alternative co-action between the plunger (2) and the piston (3). The plunger 2 provides a sealing surface (2.6) and a face (2.7) that locates the spring (4). The plunger head (2.8) has an inward facing lip (2.9) which lodges against the triangular section ring (3.2).

Figure 7:
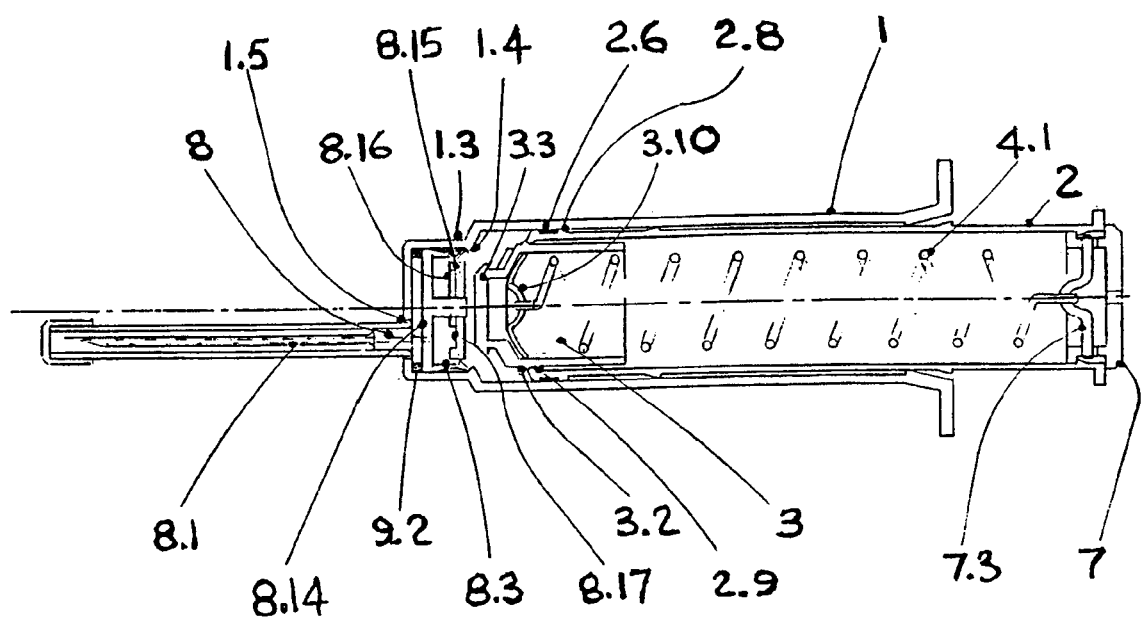
FIG. 7 illustrates a sixth embodiment of the syringe having a needle offset from the longitudinal axis of the syringe and in which the plunger is about to engage the needle carrier.

FIG. 7 shows a typical construction in which the needle (8.1) is offset from the centre line. The housing (1) has a nose (1.3) of reduced diameter with an aperture (1.5) through the end wall.

The needle carrier (8) has the needle (8.1) eccentrically positioned and aligned with the aperture (1.5). The flange (8.14) has a reduced diameter which carries the 'O' seal ring (9.2) and the claw ended arms (8.3) which are held in engagement with the lip (1.4) by a spring ring (8.15) which has a recess (8.16) and one or more cut-outs (8.17).

The piston (3) has a triangular section annular ridge (3.2) on the outer cylindrical surface. The piston (3) terminates in a head (3.3).

A sprung anchor (3.10) is fitted inside the piston (3). A separate anchor (7.3) is attached to the plunger closure piece (7). The spring (4.1) is attached at both ends to the anchors (3.10) and (7.3).

The plunger has a sealing surface (2.6) and the plunger head (2.8) has an inward facing lip (2.9). The inward lip (2.9) lodges against the triangular section annular ridge (3.2) thereby holding the spring (4.1) in tension.

Figure 8:
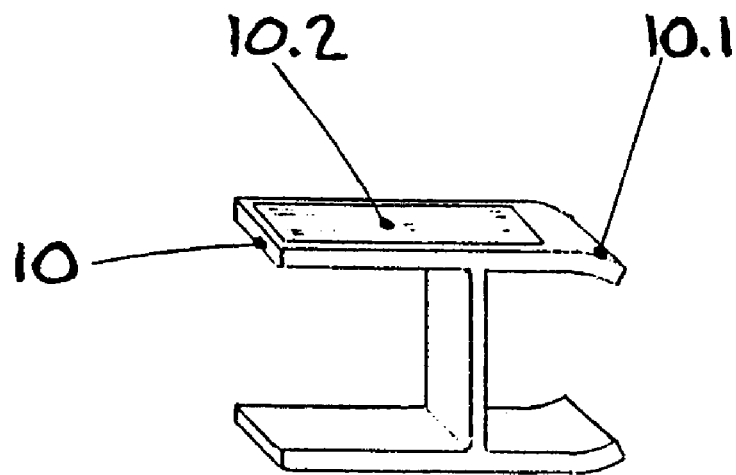
FIG. 8 illustrates a plunger stop for attachment to an exposed length of the plunger.

FIG. 8 shows a plunger stop (10) with suitably radiused members (10.1) to fit over the exposed length of the plunger (2) between the flanges (1.1) and (2.1) as shown in FIG. 1. The length of the stop will be dependent upon whether it is being used to prevent accidental needle retraction before use or to prevent accidental discharge of pre-loaded injectant. The members are capable of having a label (10.2) attached.

Figure 9:
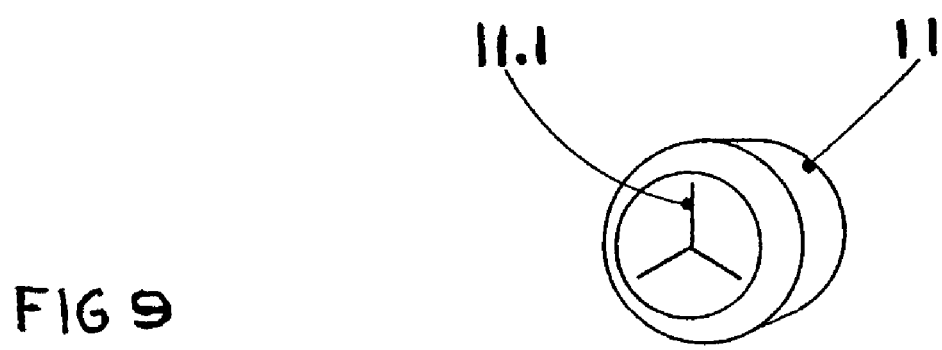
FIG. 9 illustrates an anti-drip cap for attachment to the syringe nose.
Figure 1:
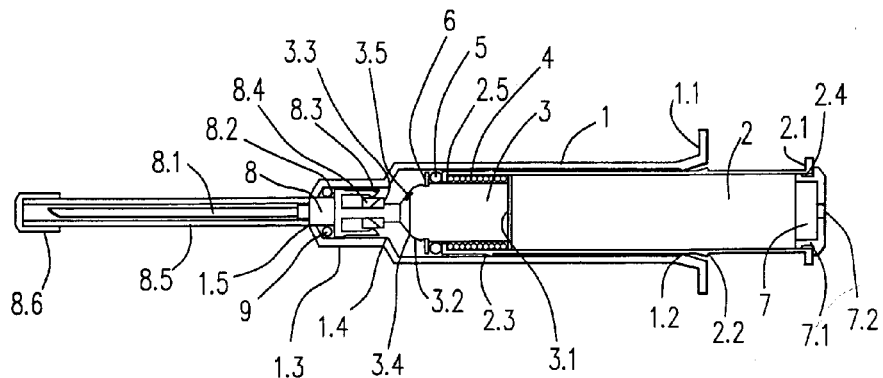
Figure 1A:
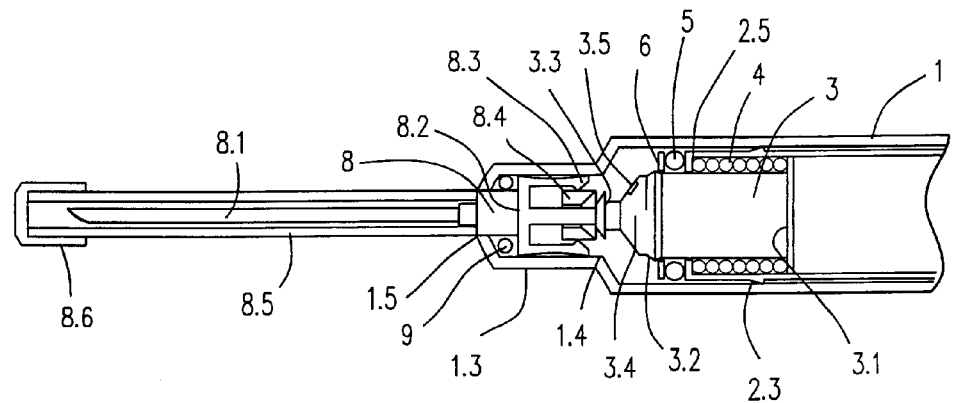
Figure 2:
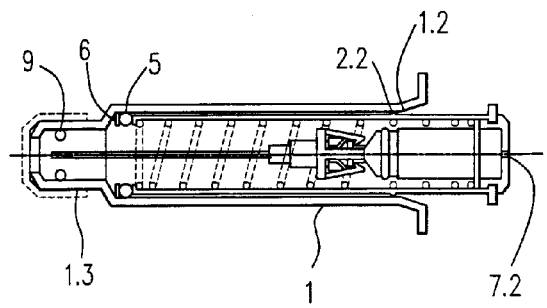
Figure 3:
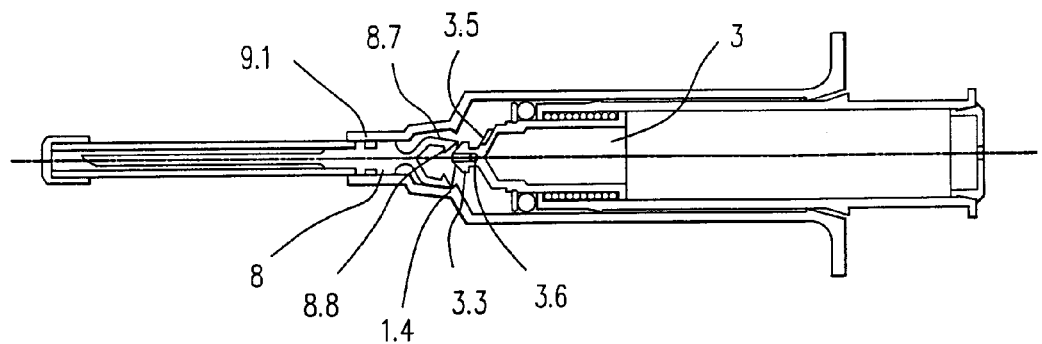
Figure 4:
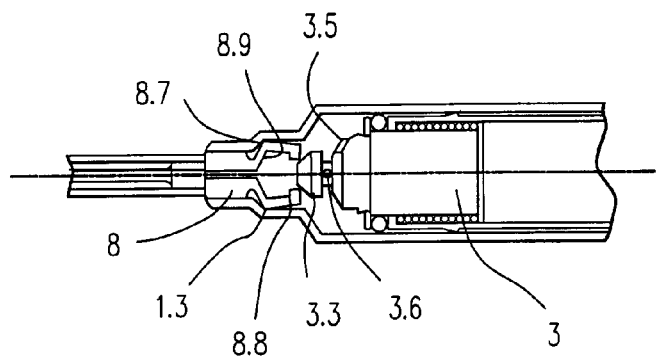
Figure 5:
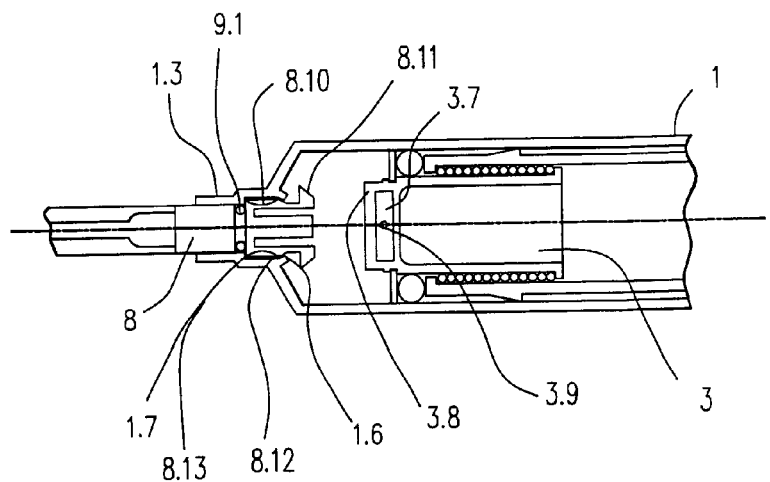
Figure 6:
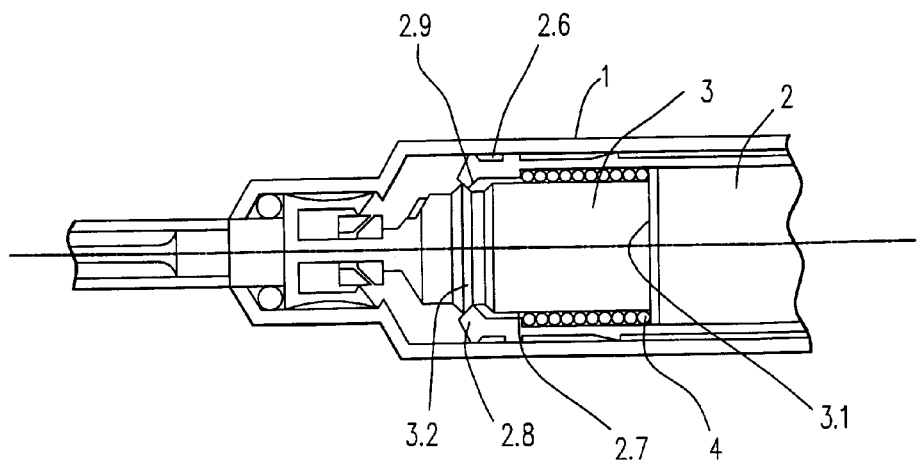
Figure 7:
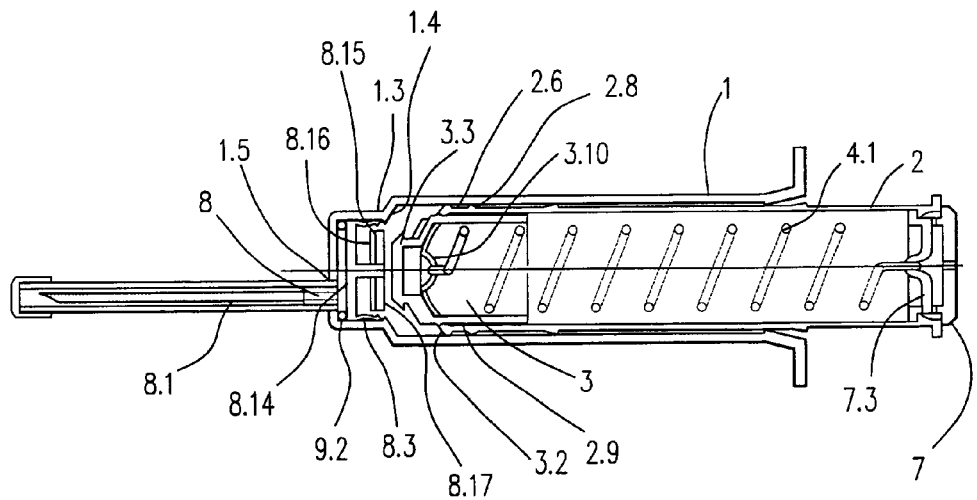
Figure 8:
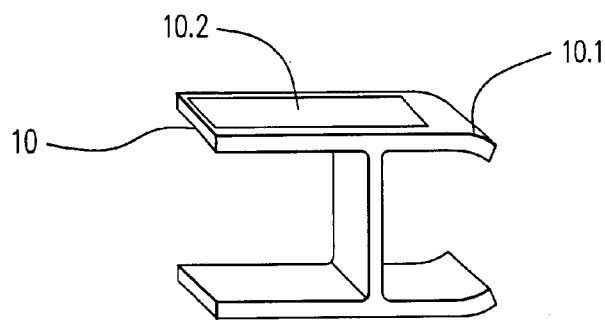
Figure 9:
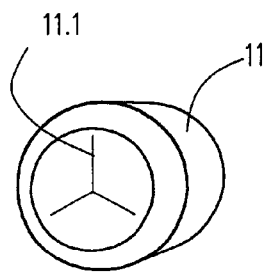
Figure 1:
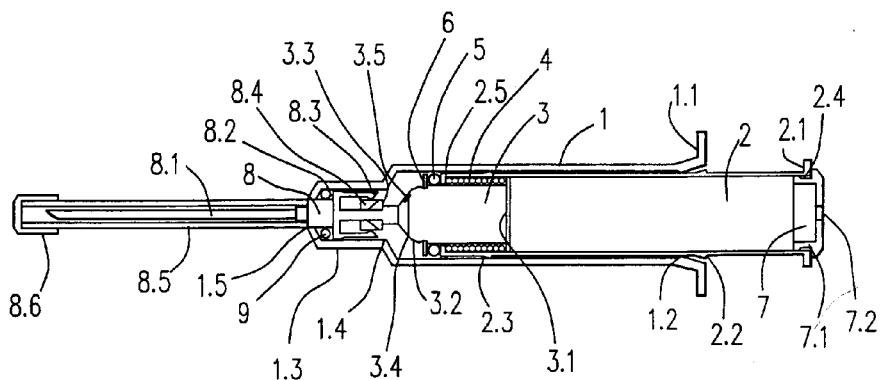
Figure 1A:
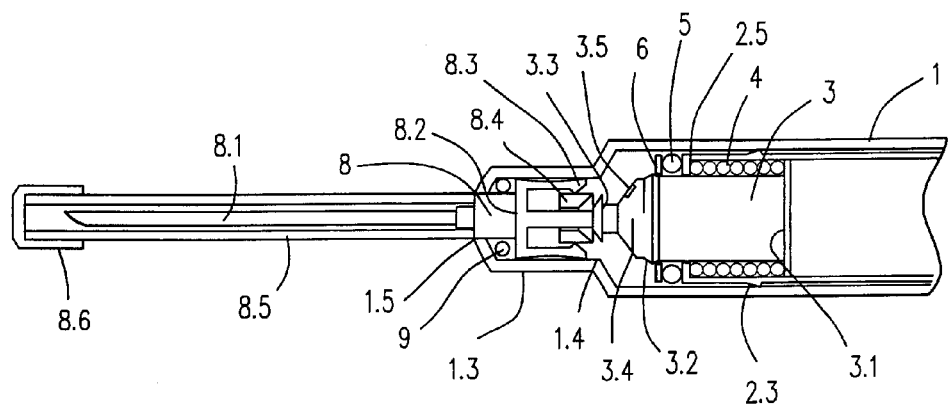
Figure 2:
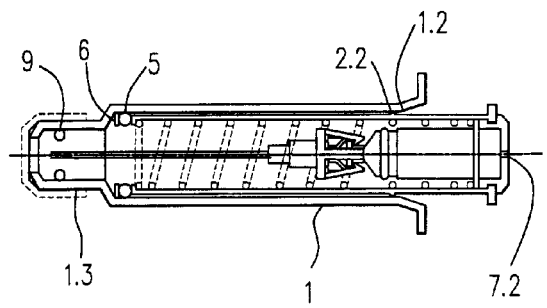
Figure 3:
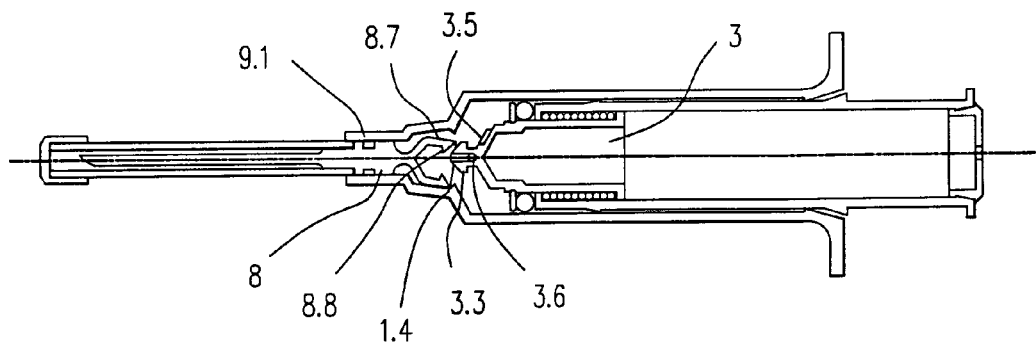
Figure 4:
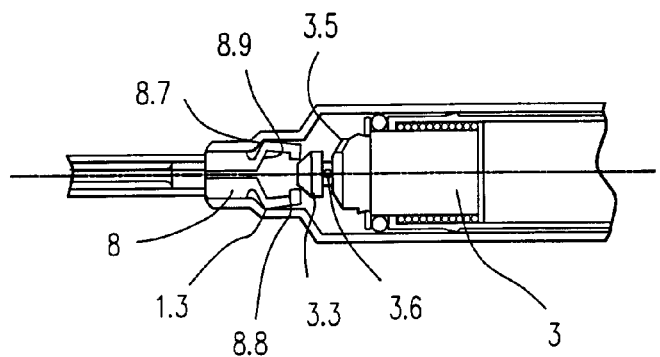
Figure 5:
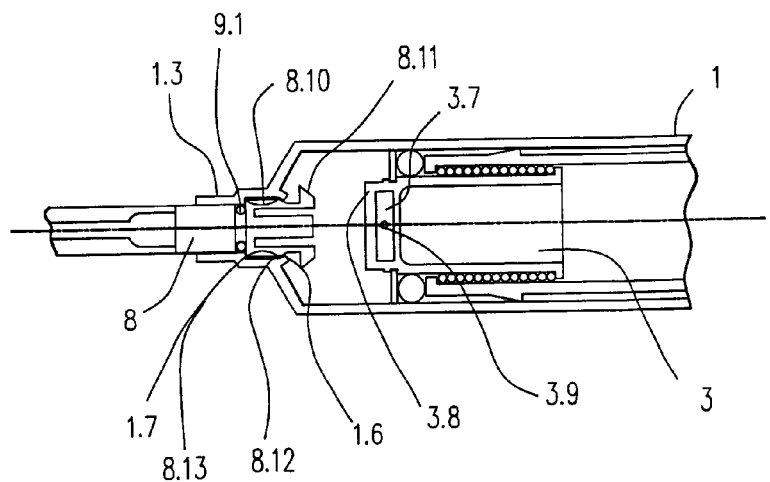
Figure 6:
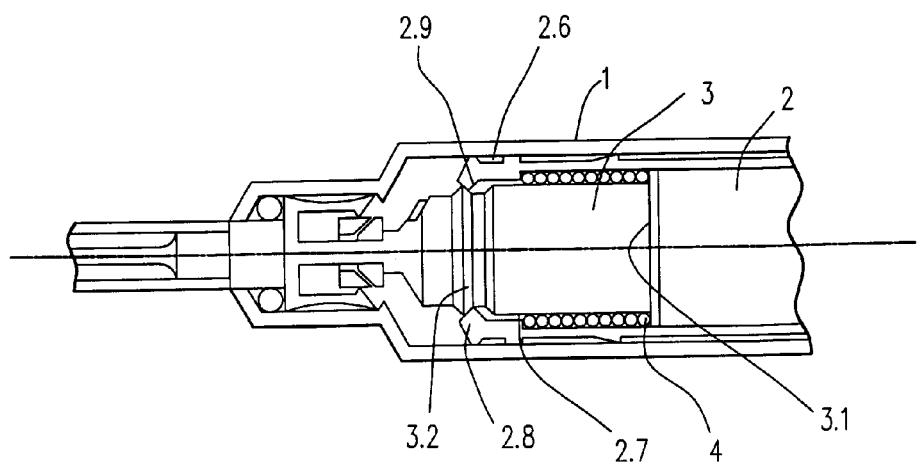
Figure 7:
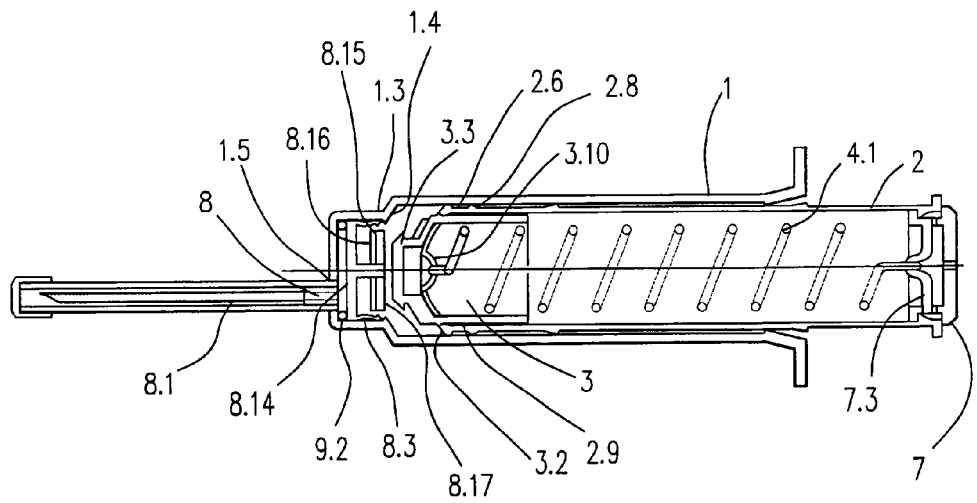
Figure 8:
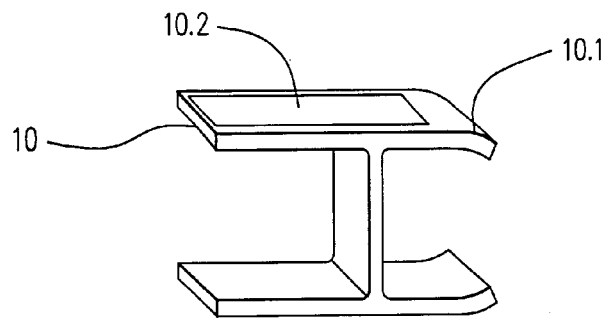
Figure 9:
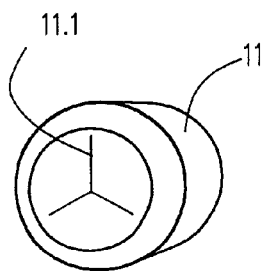

FIG. 9 shows an anti-drip cap (11) designed to fit over the syringe nose (1.3) (shown in FIG. 1). The substantially flat end is split to form segments (11.1) which are flexible to allow the passage of the needle sheath (8.5) (shown in FIG. 1) during assembly and also to re-close after needle retraction. A similar cap may be provided un-segmented when capping after needle retraction is required.

Operation of the syringe follows the established practice for disposable syringes. When the operator is charging the syringe, over extension of the plunger (2) is prevented by the interaction of the rings (1.2) and (2.3). On completion of the injection stroke, automatic needle retraction is triggered by continued pressure on the plunger. Description of this operation follows and is with reference to FIGS. 1 and 2.

When the piston shoulder (3.4) meets the end wall of the housing (1), the piston head (3.3) has entered between the clawed arms (8.3) of the needle carrier (8) and displaced the spring ring (8.4), allowing the clawed arms (8.3) to snap onto the piston head (3.3) providing positive attachment with some angular freedom to ensure positive needle retraction. The fluid bypass (3.5) ensures freedom from fluid lock.

Further pressure on the plunger (2) against the now stationary piston (3), dislodges the retaining ring (6), freeing the spring (4) to snap the needle carrier (8) into the plunger (2) and to retain it therein.

Figure 2:
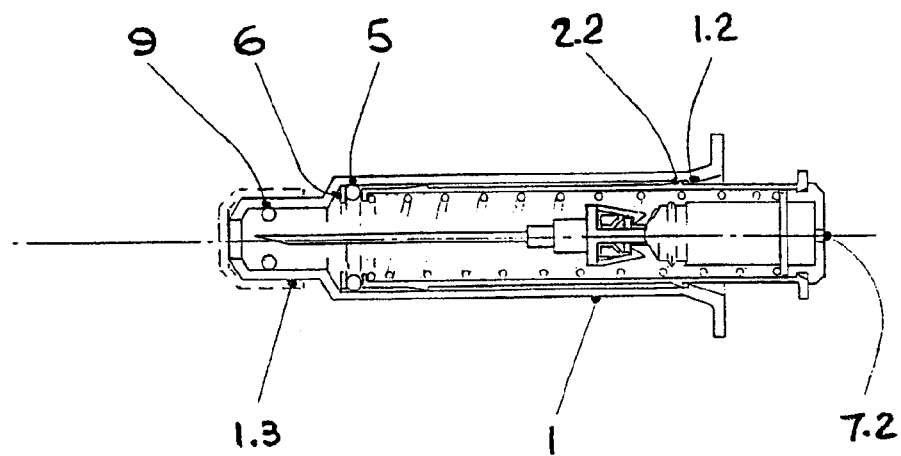
FIG. 2 illustrates the syringe shown in FIG. 1 after retraction of the needle carrier.

FIG. 2 shows the syringe after needle retraction. As shown, the 'O' seals (9) and (5) and the retaining ring (6) remain at the nose end (1.3) of the housing (1), ensuring minimum friction during needle retraction. Release path for air is afforded by the plunger closure piece orifice (7.2). During the injection stroke the wedge section ring (2.2) snaps past the co-acting wedge ring (1.2) thereby preventing re-extension of the plunger.

The optional un-segmented end cap is, if required, now fitted over the nose (1.3).

Operation of a syringe containing an alternative construction of the needle carrier as described with reference to FIGS. 3, 4 and 5, is essentially as outlined with reference to FIGS. 1 and 2.

FIG. 3 shows a revised needle carrier (8) of resilient material with a cup (8.7) displaced from the centre line of the syringe so as to latch behind the lip (1.4) during assembly. Near the end of the injection stroke the piston head (3.3)

centralises the cup (8.7) which snaps behind the retaining lip (8.8) disengaging the cup (8.7) from the lip (1.4). The fluid bypass (3.5) and the fluid passage (3.6) ensure freedom from fluid lock. Needle retraction follows the sequence described with reference to FIGS. 1 and 2 except that the needle seal (9.1) remains in the needle carrier (8).

FIG. 4 shows a needle carrier (8) of resilient material with a cup (8.7) in firm ring contact with a cylindrical section of the nose (1.3) obviating the need for a seal. During operation any end load on the needle tends to flatten the dished area (8.9) increasing the radial load against the cylindrical portion of the nose (1.3), preventing axial movement and making additional locking unnecessary. At the end of the injection stroke, when the piston head (3.3) enters the cup (8.7) it is retained by the lip (8.8). Subsequent pull on the cup during needle retraction tends to elongate the cup, reducing its radial pressure against the nose (1.3) allowing free movement. The fluid bypass (3.5) and the fluid passage (3.6) ensure freedom from fluid lock. Needle retraction follows the sequence as described with reference to FIGS. 1 and 2 except for the absence of the 'O' seal (9).

FIG. 5 shows a needle carrier (8) with outwardly sprung arms (8.10) with catches (8.12) such that on insertion into the housing (1), the catches (8.12) snap behind the lip (1.6) to lock the needle carrier (8) in position.

Towards the end of the injection stroke the piston cup end (3.7) passes over claw ends (8.11) closing the arms (8.10) and disengaging the catches (8.12) from the lip (1.6) and connecting the claw ends (8.11) to the lip (3.8) of the piston cup end (3.7). The fluid passage (3.9) ensures freedom from fluid lock. Needle retraction follows the sequence described with reference to FIGS. 1 and 2 except that the seal (9.1) is retained in the needle carrier (8).

FIG. 6 depicts an alternative construction of the plunger seal and the dislodgeable retaining means for the piston.

In this construction the plunger (2) has a head (2.8) of sufficient resilience to effect a dynamic seal (2.6) against the inner surface of the housing (1). The head (2.8) has an inward facing lip (2.9) which co-acts with triangular section ring (3.2) of the piston (3) to effect a seal between the plunger (2) and the piston (3).

The spring (4) is compressed and retained between faces (2.7) and (3.1) by the reversible snap co-action of the triangular section ring (3.2) and the inward facing lip (2.9) of the plunger (2). At the completion of the injection stroke the inward facing lip (2.9) snaps past the triangular section ring (3.2) releasing the spring to effect needle retraction.

Needle retraction follows the sequence described with reference to FIGS. 1 and 2 except for the absence of the 'O' seal (5).

FIG. 7 shows an adaptation of the invention in which the needle is offset from the centre line of the syringe in order to meet the operational requirements of larger capacity syringes.

To allow the maximum eccentricity of the needle (8.1), extra space has been obtained by replacing the compression spring of the standard models with a tension spring (4.1).

Operation follows the usual procedure. Towards the end of the injection stroke the piston head (3.3) displaces the spring ring (8.15), allowing the claw ended arms (8.3) to snap onto the piston head (3.3).

To ensure continuous free fluid flow the spring ring (8.15) is recessed at (8.16) and cut away at one or more points (8.17).

When the piston (3) bottoms at the end of the stroke, continued pressure on the plunger (2) causes the inward facing lip (2.9) to override the triangular section ring (3.2), allowing the spring (4.1) to effect needle retraction.

Needle retraction generally follows the sequence as described with reference to FIGS. 1 and 2.

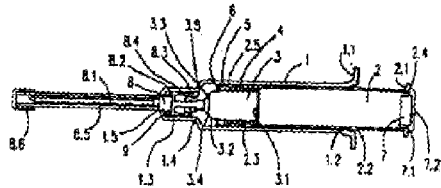

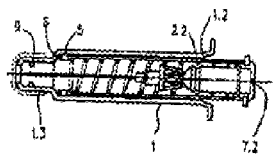

What is claimed is:

1. A hypodermic syringe including a housing, a plunger, a needle carrier with a needle mounted thereto positionable during assembly of the syringe within the housing with the needle extending therefrom, sealing means for defining a seal carrier and the housing, a sheath mounted to the needle carrier and surrounding the needle, and stored energy means, wherein the plunger and stored energy means are configured such that when the syringe is used and the plunger reaches the needle carrier, the plunger becomes attached to the needle carrier and the stored energy in the stored energy means is released to retract the needle carrier and the needle into the housing, the housing being configured such that the seal is formed between the needle carrier and the housing during assembly and such that the needle carrier with the needle mounted thereto is positionable during assembly of the syringe through the housing with the needle pre-sheathed.

2. A syringe as claimed in claim 1, wherein the plunger comprises a casing and a piston located and movable within the casing.

3. A syringe as claimed in claim 2 wherein the piston includes means for engagement with the needle carrier.

4. A syringe as claimed in claim 3 wherein the engagement means comprises either a male or female member on the head engaging with a corresponding male or female member on the needle carrier.

5. A syringe as claimed in claim 4 wherein the engagement means comprises a projection formed on the piston and the needle carrier comprises a number of spring biased arms which are retained in position by a collar, the collar being displaceable by the projection on the head such that the arms engage behind the projection thereby attaching the needle carrier to the piston.

6. A syringe as claimed in claim 3 wherein the needle carrier includes a cup which is retained in position by a lip formed on the housing, and a projection on the piston is engageable with cup so as to release the cup from engagement with the lip, and the cup has a lip which engages behind the projection thereby joining the needle carrier to the piston.

7. A syringe as claimed in claim 3 in which the needle carrier includes a number of deflectable arms which are engageable with an opening in the piston so as to join the needle carrier with the piston.

8. A syringe as claimed in claim 7 in which the needle carrier has at least one projection engaging with a lip to retain the needle carrier to the housing of the syringe prior to displacement of the deflectable arms, displacement of the deflectable arms releasing the needle carrier from the housing.

9. A syringe as claimed in claim 3 wherein the means for engagement with the needle carrier includes a fluid passage to prevent fluid lock.

10. A syringe as claimed in claim 1 wherein the stored energy means comprises a spring co-operating between the piston and the casing and having a releasable retaining means in order to release the energy stored within the spring.

11. A syringe as claimed in claim 10 wherein the releasable retaining means comprises a ring located on the piston which is disengageable from the piston as a result of pressure exerted on the plunger after completion of an injection stroke.

12. A syringe as claimed in claim 10 in which the releasable retaining means comprises a lip on the casing which co-acts with a circular ridge formed on the piston.

13. A syringe as claimed in claim 10, wherein the spring is a tension or compression spring.

14. A syringe as claimed in claim 1 wherein the plunger and the housing are formed with means for engaging one another so as to prevent removal of the plunger from the casing.

15. A syringe as claimed in claim 14 wherein the plunger is provided with at least one projection which is engageable with a corresponding lip on the housing.

16. A syringe as claimed in claim 1, wherein the sheath is provided with a cap.

17. A syringe as claimed in claim 1 wherein the housing is provided with a penetrable and self-closing cap to prevent fluid seepage.

18. A syringe as claimed in claim 1 wherein the needle axis is displaced from the centre line of the barrel.

19. A syringe as claimed in claim 1 wherein a detachable spacer capable of being labelled is located between the open end of the housing and the flanged end of the plunger so as to inhibit unwanted inward movement of the plunger.

20. A method of assembling a hypodermic syringe according to claim 1, including the steps of mounting a needle to the needle carrier, positioning the needle carrier in the housing such that the needle extends therefrom, and mounting a sheath to the needle carrier over the needle before positioning the needle carrier in the housing.

21. A syringe as claimed in claim 1, wherein the sealing means comprises an O-ring seal.

22. A syringe as claimed in claim 1, wherein the sealing means comprises engagement between the needle carrier and the housing.

23. A method of assembling a hypodermic syringe, comprising:
 (a) mounting a needle to a needle carrier;
 (b) positioning the needle carrier and needle through and in a housing such that the needle extends from the housing;
 (c) forming a seal between the needle carrier and the housing during step (b); and
 (d) mounting a sheath to the needle carrier over the needle before performing step (b).

24. A hypodermic syringe assembled according to the method of claim 23, wherein step (c) is effected by sealing means for defining the seal between the needle carrier and the housing.

25. A method of assembling a hypodermic syringe, comprising:
 (a) mounting a needle to a needle carrier;
 (b) mounting a sheath over said needle; and
 (c) locating the needle carrier within a housing comprising first and second spaced apertures by inserting the needle carrier with the needle and the needle sheath mounted thereto through the first aperture and positioning the needle carrier such that the needle with the needle sheath thereon extends externally of the housing from said second aperture.

26. A hypodermic syringe assembled according to the method of claim 25 and further comprising sealing means for defining a seal between the needle carrier and the housing.

* * * * *

UNITED STATES PATENT AND TRADEMARK OFFICE
CERTIFICATE OF CORRECTION

PATENT NO. : 6,706,019 B1  Page 1 of 6
DATED : March 16, 2004
INVENTOR(S) : Parker et al.

It is certified that error appears in the above-identified patent and that said Letters Patent is hereby corrected as shown below:

The title page, showing illustrative figures should be deleted and substitute therefore the attached title page.

Drawings,
Delete drawings Sheet 1, 1A and 2-9, and substitute therefor, the drawing sheets consisting of Figs. 1, 1A and 2-9 as shown on the attached pages.

Signed and Sealed this

Twenty-fourth Day of August, 2004

JON W. DUDAS
*Director of the United States Patent and Trademark Office*

(12) United States Patent
Parker et al.

(10) Patent No.: US 6,706,019 B1
(45) Date of Patent: Mar. 16, 2004

(54) HYPODERMIC SYRINGES

(76) Inventors: David W. Parker, 4 Kimble Close, Bury, Lancashire (GB), BL8 4QQ; Colin H. Burgess, 45 Holcombe Lee, Ramsbottom, Lancashire (GB), BL0 9QR (*) Notice: Subject to any disclaimer, the term of this patent is extended or adjusted under 35 U.S.C. 154(b) by 0 days.

(21) Appl. No.: 09/787,813

(22) PCT Filed: Sep. 22, 1999

(86) PCT No.: PCT/GB99/03170
§ 371 (c)(1),
(2), (4) Date: May 17, 2001

(87) PCT Pub. No.: WO00/18454
PCT Pub. Date: Apr. 6, 2000

(30) Foreign Application Priority Data

Sep. 25, 1998 (GB) .............................................. 9820784

(51) Int. Cl.[7] .............................. A61M 5/32; A61M 5/00
(52) U.S. Cl. ........................ 604/198; 604/110; 128/919
(58) Field of Search .................................. 604/198, 192, 604/110, 220, 194, 187; 128/919

(56) References Cited

U.S. PATENT DOCUMENTS

| | | | | |
|---|---|---|---|---|
| 5,114,404 A | * | 5/1992 | Paxton et al. | 604/110 |
| 5,122,118 A | * | 6/1992 | Haber et al. | 128/919 |
| 5,135,511 A | * | 8/1992 | Houghton et al. | 604/218 |
| 5,211,628 A | | 5/1993 | Marshall | |
| 5,324,265 A | | 6/1994 | Murray et al. | |
| 5,344,403 A | | 9/1994 | Lee | |
| 5,378,240 A | * | 1/1995 | Curie et al. | 604/110 |
| 5,423,758 A | * | 6/1995 | Shaw | 600/576 |
| 5,458,576 A | | 10/1995 | Haber et al. | |
| 5,624,405 A | * | 4/1997 | Futagawa et al. | 604/187 |
| 5,632,733 A | * | 5/1997 | Shaw | 604/110 |
| 5,782,804 A | * | 7/1998 | McMahon | 128/919 |
| 5,885,257 A | * | 3/1999 | Badger | 604/110 |
| 5,997,511 A | * | 12/1999 | Curie et al. | 604/110 |
| 6,096,005 A | * | 8/2000 | Botich et al. | 604/110 |

FOREIGN PATENT DOCUMENTS

| | | |
|---|---|---|
| EP | 0 505 330 | 9/1992 |
| EP | 0 636 381 | 2/1995 |
| EP | 0 747 075 | 12/1996 |
| WO | WO90/06146 | 6/1990 |
| WO | WO91/03269 | 3/1991 |
| WO | WO93/07923 | 4/1993 |
| WO | WO95/11713 | 5/1995 |
| WO | WO96/05879 | 2/1996 |
| WO | WO96/27403 | 9/1996 |

* cited by examiner

*Primary Examiner*—Manuel Mendez
*Assistant Examiner*—Mark K. Han
(74) *Attorney, Agent, or Firm*—Nixon & Vanderhye P.C.

(57) ABSTRACT

A disposable hypodermic syringe, which is provided with the needle fitted and sheathed, provides automatic retraction of the needle after use. The syringe may be supplied precharged with an injectant. The completion of the injection stroke attaches the piston to the needle carrier and subsequently dislodges a retaining ring thereby freeing the piston from the plunger and releasing stored energy of a spring or the like to draw the piston and needle carrier into the plunger. The plunger is positively retained inside the housing by the interaction of rings. Alternative methods of locating the needle carrier during use and of attaching the piston to the needle carrier to enable retraction are shown. An alternative method of retaining the piston on the plunger is also shown. A further configuration is shown affording the use of an offset needle. The syringe has optional features to prevent unwanted inward movement of the plunger and to prevent seepage of liquid after use.

26 Claims, 6 Drawing Sheets

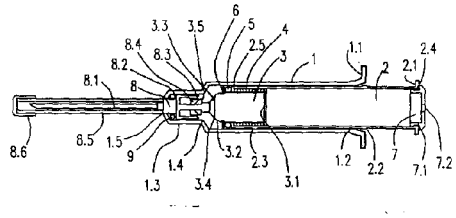

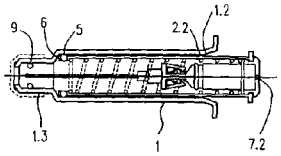

UNITED STATES PATENT AND TRADEMARK OFFICE
CERTIFICATE OF CORRECTION

| | |
|---|---|
| PATENT NO. | : 6,706,019 B1 |
| APPLICATION NO. | : 09/787813 |
| DATED | : March 16, 2004 |
| INVENTOR(S) | : Parker et al. |

It is certified that error appears in the above-identified patent and that said Letters Patent is hereby corrected as shown below:

The title page, showing illustrative figures should be deleted and substitute therefore the attached title page.

<u>Drawings,</u>
Delete drawings Sheet 1, 1A and 2-9, and substitute therefor, the drawing sheets consisting of Figs. 1, 1A and 2-9 as shown on the attached pages.

This certificate supersedes the Certificate of Correction issued August 24, 2004.

Signed and Sealed this

Third Day of March, 2009

JOHN DOLL
*Acting Director of the United States Patent and Trademark Office*

(12) United States Patent
Parker et al.

(10) Patent No.: US 6,706,019 B1
(45) Date of Patent: Mar. 16, 2004

(54) HYPODERMIC SYRINGES

(76) Inventors: David W. Parker, 4 Kimble Close, Bury, Lancashire (GB), BL8 4QQ; Colin H. Burgess, 45 Holcombe Lee, Ramsbottom, Lancashire (GB), BL0 9QR (*) Notice: Subject to any disclaimer, the term of this patent is extended or adjusted under 35 U.S.C. 154(b) by 0 days.

(21) Appl. No.: 09/787,813
(22) PCT Filed: Sep. 22, 1999
(86) PCT No.: PCT/GB99/03170
§ 371 (c)(1), (2), (4) Date: May 17, 2001
(87) PCT Pub. No.: WO00/18454
PCT Pub. Date: Apr. 6, 2000

(30) Foreign Application Priority Data

Sep. 25, 1998 (GB) .................................. 9820784

(51) Int. Cl.⁷ .......................... A61M 5/32; A61M 5/00
(52) U.S. Cl. .................... 604/198; 604/110; 128/919
(58) Field of Search ........................... 604/198, 192, 604/110, 220, 194, 187; 128/919

(56) References Cited

U.S. PATENT DOCUMENTS

| | | | |
|---|---|---|---|
| 5,114,404 A * | 5/1992 | Paxton et al. | 604/110 |
| 5,122,118 A * | 6/1992 | Haber et al. | 128/919 |
| 5,135,511 A * | 8/1992 | Houghton et al. | 604/218 |
| 5,211,628 A | 5/1993 | Marshall | |
| 5,324,265 A | 6/1994 | Murray et al. | |
| 5,344,403 A | 9/1994 | Lee | |
| 5,378,240 A * | 1/1995 | Curie et al. | 604/110 |
| 5,423,758 A * | 6/1995 | Shaw | 600/576 |
| 5,458,576 A | 10/1995 | Haber et al. | |
| 5,624,405 A * | 4/1997 | Futagawa et al. | 604/187 |
| 5,632,733 A * | 5/1997 | Shaw | 604/110 |
| 5,782,804 A * | 7/1998 | McMahon | 128/919 |
| 5,885,257 A * | 3/1999 | Badger | 604/110 |
| 5,997,511 A * | 12/1999 | Curie et al. | 604/110 |
| 6,096,005 A * | 8/2000 | Botich et al. | 604/110 |

FOREIGN PATENT DOCUMENTS

| | | |
|---|---|---|
| EP | 0 505 330 | 9/1992 |
| EP | 0 636 381 | 2/1995 |
| EP | 0 747 075 | 12/1996 |
| WO | WO90/06146 | 6/1990 |
| WO | WO91/03269 | 3/1991 |
| WO | WO93/07923 | 4/1993 |
| WO | WO95/11713 | 5/1995 |
| WO | WO96/05879 | 2/1996 |
| WO | WO96/27403 | 9/1996 |

* cited by examiner

Primary Examiner—Manuel Mendez
Assistant Examiner—Mark K. Han
(74) Attorney, Agent, or Firm—Nixon & Vanderhye P.C.

(57) ABSTRACT

A disposable hypodermic syringe, which is provided with the needle fitted and sheathed, provides automatic retraction of the needle after use. The syringe may be supplied pre-charged with an injectant. The completion of the injection stroke attaches the piston to the needle carrier and subsequently dislodges a retaining ring thereby freeing the piston from the plunger and releasing stored energy of a spring or the like to draw the piston and needle carrier into the plunger. The plunger is positively retained inside the housing by the interaction of rings. Alternative methods of locating the needle carrier during use and of attaching the piston to the needle carrier to enable retraction are shown. An alternative method of retaining the piston on the plunger is also shown. A further configuration is shown affording the use of an offset needle. The syringe has optional features to prevent unwanted inward movement of the plunger and to prevent seepage of liquid after use.

26 Claims, 4 Drawing Sheets